(12) United States Patent
Johnson (10) Patent No.: US 7,395,292 B2
(45) Date of Patent: Jul. 1, 2008

(54) METHOD FOR DISPLAYING SPECTRAL TRENDS IN COMPLEX SIGNALS

(76) Inventor: Mark W. Johnson, 2836 Corydon Rd., Cleveland Hts, OH (US) 44118

( * ) Notice: Subject to any disclaimer, the term of this patent is extended or adjusted under 35 U.S.C. 154(b) by 791 days.

(21) Appl. No.: 10/962,336

(22) Filed: Oct. 8, 2004

(65) Prior Publication Data

US 2005/0080828 A1    Apr. 14, 2005

Related U.S. Application Data

(60) Provisional application No. 60/509,702, filed on Oct. 8, 2003.

(51) Int. Cl.
*G06F 15/00* (2006.01)
*G06F 19/00* (2006.01)

(52) U.S. Cl. .......................... 708/403; 702/26
(58) Field of Classification Search ............... 708/403, 708/404, 405; 702/76
See application file for complete search history.

(56) References Cited

U.S. PATENT DOCUMENTS

| | | | |
|---|---|---|---|
| 6,050,940 A | 4/2000 | Braun et al. | |
| 6,224,549 B1 | 5/2001 | Drongelen | |
| 6,390,983 B1 * | 5/2002 | Mo et al. | 600/453 |
| 6,714,605 B2 * | 3/2004 | Sugar et al. | 375/340 |
| 6,735,467 B2 | 5/2004 | Wilson | |
| 2004/0181162 A1 | 9/2004 | Wilson | |
| 2004/0199482 A1 | 10/2004 | Wilson | |

OTHER PUBLICATIONS

Cadwell Laboratories, Inc., Excel CSA Program Description, 7 pages, www.cadwell.com.
Cooley, James and Tukey, John; An Algorithm for the Machine Claculation of Complex Fourier Series; Aug. 17, 1964; pp. 297-301.
Grass, Albert and Biggs, Frederic; A Fourier Transform of the Electroencephalogram; Jul. 29, 1938; pp.
Salinsky, Sutula, Roscoe; Abstract of Representation of Sleep Stages by Color Density Spectral Array; Jun. 1987, 1 page.

* cited by examiner

*Primary Examiner*—Chuong D Ngo (57) ABSTRACT

A method for displaying changes in spectral content of data signals over periods of time using a computer system. The method includes the steps of transforming time segments of digitized data signals into a frequency based spectral representation of the digitized data. The resulting spectral data are then grouped into appropriate frequency bins. Each frequency bin is normalized by the frequency range of the bin. The energy or power in each frequency bin is then multiplied by $f^n$, where f represents an estimate of the frequency of the bin, and n is an exponent which is used to normalize the frequency content of the data. A logarithmic value is then calculated for each frequency bin. The logarithmic value of each frequency bin for each time period is then mapped to a color or gray-scale value. Finally, the mapped color or gray-scale value is displayed on a computer monitor in the computer system as an image, where the signal frequency is represented along one axis, time is represented along a second axis, and the value of the energy or power at that given time and frequency is displayed as the color or gray-scale value assigned to that point.

4 Claims, 11 Drawing Sheets
(3 of 11 Drawing Sheet(s) Filed in Color)

METHOD FOR DISPLAYING SPECTRAL TRENDS IN COMPLEX SIGNALS

CROSS-REFERENCE TO RELATED APPLICATIONS

The present application claims priority from U.S. patent application Ser. No. 60/509,702 filed Oct. 8, 2003, the entire subject matter of which is incorporated herein by reference.

BACKGROUND OF THE INVENTION

1. Field of Invention

The present invention relates to computer display techniques used in connection with data analysis, and more specifically to a method and system for displaying spectral trends in complex signals.

2. Background of the Related Art

The history of techniques developed for data analysis of biological and non-biological signals is well documented. The French mathematician and physicist Jean Baptiste Joseph Fourier originated Fourier's theorem on vibratory motion and the Fourier series around 1800. This provided a method for representing discontinuous functions by a trigonometric series. In 1938, A. M. Grass and F. A. Gibbs published "A Fourier transform of the electroencephalogram (EEG)" in the *Journal of Neurophysiology*.

Prior to this pioneering work, the electrical signals produced by the brain were displayed only as signals fluctuating over time. Using the Fourier transform, a 30 second segment of EEG was redisplayed, showing the relative amount of EEG energy present at different frequencies. This "pre-computer" era application used a combination of photographic, mechanical, and electronic apparatus to construct a graphical representation of the Fourier transform.

In the later half of the $20^{th}$ century, the development of the digital computer greatly simplified the conversion of biological EEG signals into their corresponding frequency spectra. In 1965, J. W. Cooley and J. W. Tukey published "An algorithm for the machine computation of complex Fourier series" in *Mathematical Computation*. Their algorithm, known as the Fast Fourier Transform (FFT), reduced to practice an algorithm that was practical for computing the frequency spectrum of any digitized signal. Many people, research publications, and text books have described methods for calculating the frequency spectrum of a signal. The complicated nature of the FFT, which has many subtleties that cannot be ignored, is well documented in such references.

From the late 1960s through the late 1980s, many researchers were using digitized EEGs, and publishing a wide variety of analyses, including spectral analysis. In the late 1980s through the early 1990s, most of the major electroencephalograph manufacturers introduced digital electroencephalographs. For example, Schwartzer GmbH (1988), Nihon Kohden (1991), Astromed-Grass (now Grass-Telefactor), Nicolet Biomedical (now Viasys), Stellate Systems, Biologic Systems, Cadwell Laboratories, Oxford Instruments, all offered products. With the explosion of digital electroencephalographs, software for displaying and processing EEG also emerged. Products were offered, for example, by Persyst Development Corp. and MEGIS Software GmbH.

The techniques for calculating or displaying the spectral content of a signal are generally applied to a short and/or finite segment of data. EEG data is often collected for longer time segments, such as many hours or days. Compressed Spectral Array (CSA) is one technique that has been used to display spectral data over longer segments of time.

In 1976, G. Astaldi et. al. published "Clinical use of "compressed spectral array" in *Riv. Neurology*. The CSA technique takes individual power spectral density graphs or "frames", and "stacks" a whole sequence of them in front of each other, with a slight vertical and/or horizontal shift between each frame. The effect is a pseudo three-dimensional visual effect; like looking at a mountain landscape or a contour map, with time running along one axis, and frequency running along a second axis. The CSA technique can use color or gray scales to highlight the individual lines, but that is not required. The CSA technique is effective for visualizing spectral changes over moderate time periods, but tends to be uninterpretable over very long time periods. CSA also requires a lot of display screen space.

In 1987, M. Salinsky introduced the technique of displaying EEG using color density spectral array (cDSA) in an article called "Representation of sleep stages by color density spectral array" in *Electroencephalogr Clin. Neurophysiol*. cDSA maps the logarithm of the EEG power in each frequency bin and at each epoch, or time period, to a color. For example, red could represent the highest level, orange somewhat less, and so on, through the color spectrum, yellow, green, blue, and violet, with violet being the lowest level. The cDSA technique can also use gray scale mapping instead of color mapping, but shows changes more strikingly in color. Since its introduction, many EEG manufacturers have adopted cDSA as a tool for displaying long-term trends in EEG data (for example, Persyst, Nihon Kohden, Viasys-Nicolet, MEGIS, Cadwell, and SpaceLabs).

Currently, cDSA is the method widely used within the industry to display long term (hours to days in time) biological signals such as spectral EEG data. Unfortunately, cDSA display is limited by the nature of the signals being analyzed. Specifically, the power in the EEG signal drops precipitously as frequency increases.

In standard cDSA display, the low frequencies are red in color, and the color gradually shifts through the color spectrum to orange, yellow, etc., to violet, as the frequency of the signal increases. While it is possible to see changes in the cDSA display over longer time periods, the changes are not particularly sensitive to changes in the relative spectral content of the EEG signal. Rather, the changes are PRIMARILY sensitive to the overall amplitude of the EEG signal, with a very secondary sensitivity to changes in the shape of the spectral density curves. This drop in spectral power is commonly referred to as a "1/f power law", because the power tends to drop proportional to the frequency, f, raised to a power.

This limitation of the cDSA display, due to the drop in spectral signal power, is overcome by the method for display of the present application, which is referenced as the "modified color density spectral array" (mcDSA) or "modified gray density spectral array" (mgDSA) or as the closely related "modified compressed spectral array" (mCSA). Additionally, standard spectral analysis techniques are all improved and extended by the present method of display disclosed here.

SUMMARY OF THE INVENTION

The present application provides an improved method for displaying spectral trends in complex signals, and in particular in for long term spectral trends in complex signals.

Figure 4:
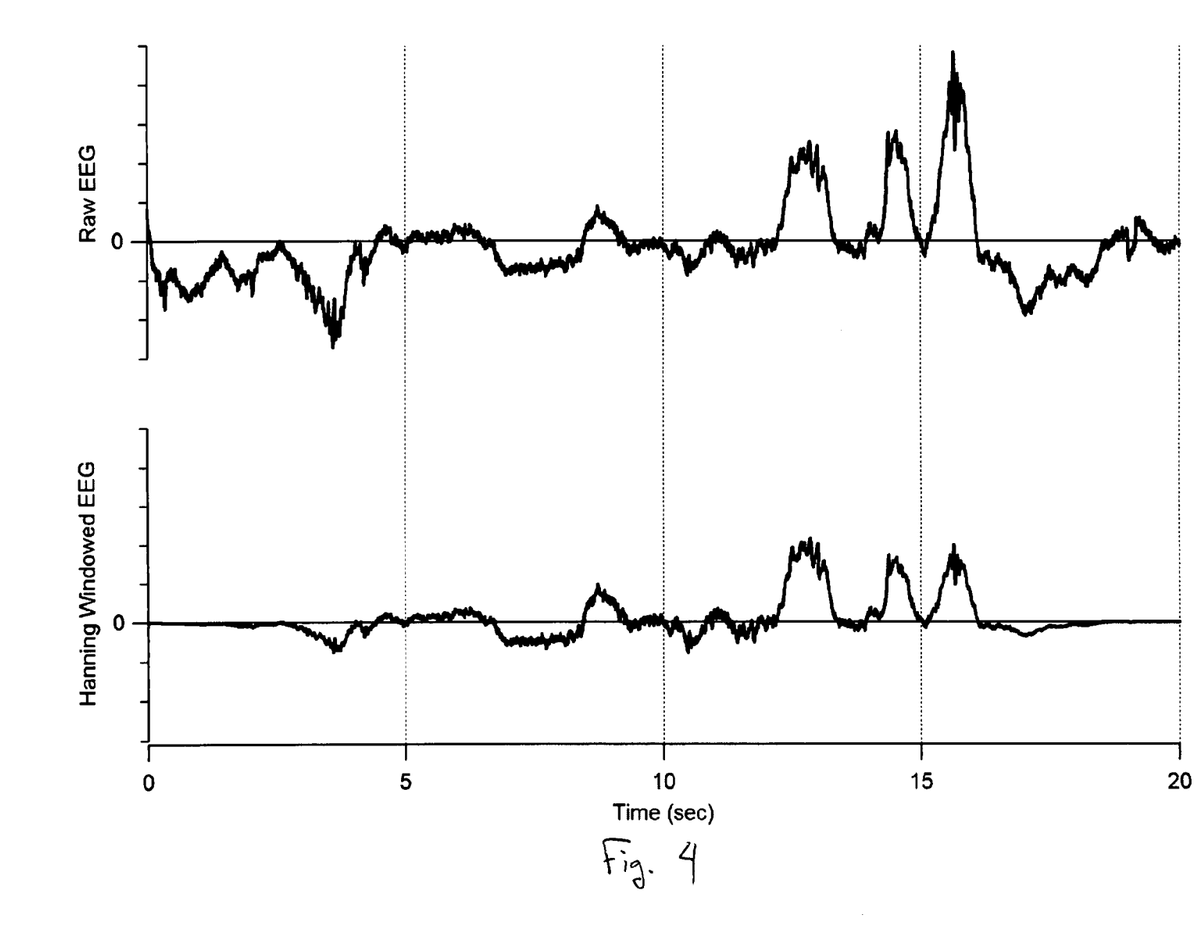
FIG. 4 shows a graph of a 20 second segment of raw EEG signal data and a graph of the same EEG signal data windowed using Hanning's windowing technique.

Many people, research publications, and text books have described methods for calculating the frequency spectrum of a signal. The complicated nature of the FFT, which has many subtleties that cannot be ignored, is well documented in such references. Additionally, and as previously mentioned, the historical techniques for calculating or displaying the spectral content of a signal are generally known, and have been applied to shorter/finite segments of data. An example of a 20 second segment of raw EEG data is shown in FIG. 4.

Figure 5:
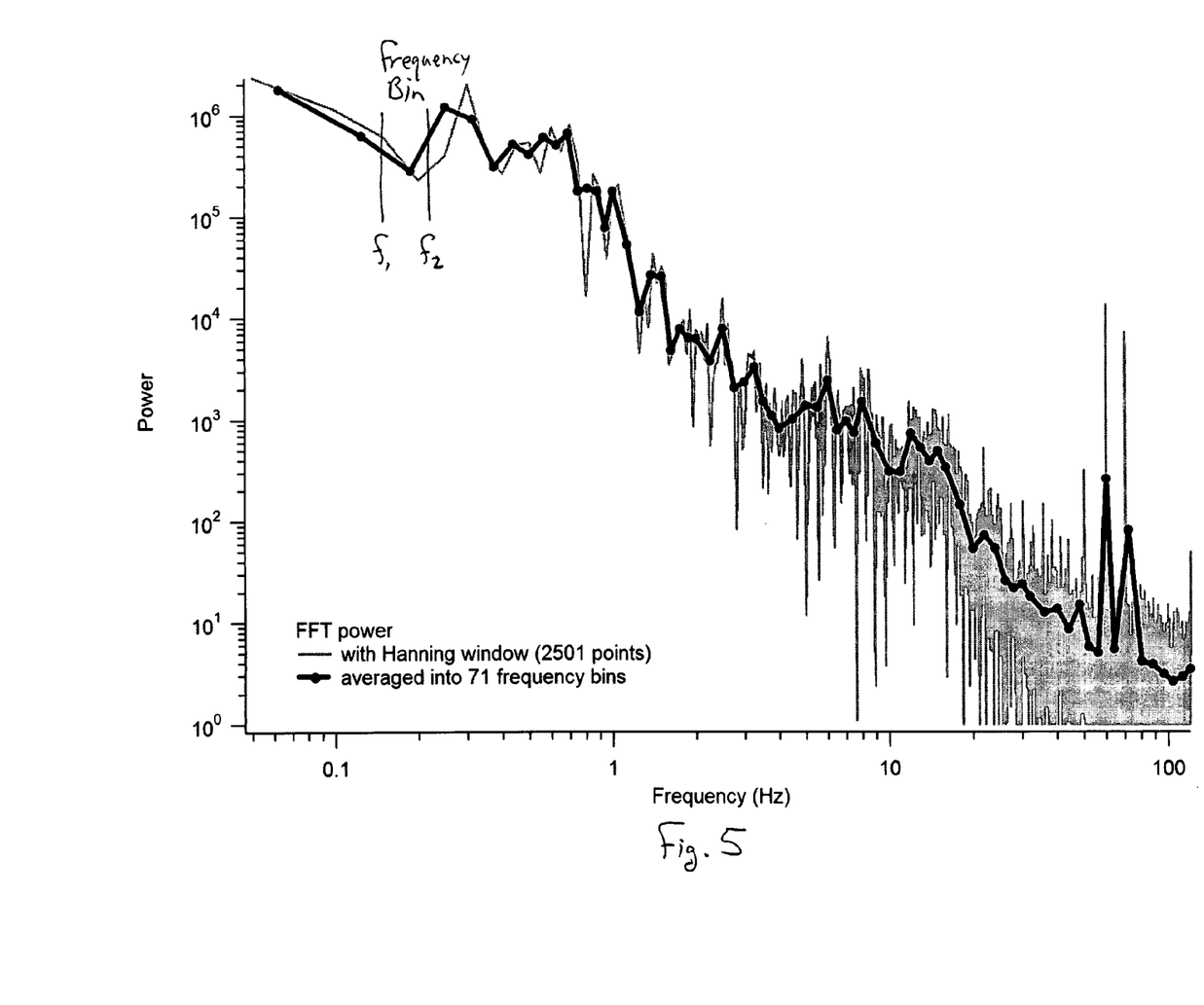
FIG. 5 shows a graph of FFT of the FIG. 4 EEG signal data modified using Hanning's technique (shown in gray) and the FFT spectrum averaged in 71 frequency bins spanning the frequency range in approximately logarithmic intervals (shown in black).

Briefly, one of the issues with respect to spectral analysis is that the FFT tends to be sensitive to certain types of artifacts. The FFT tends to be very "noisy" or "variable" at higher frequencies. As a result, "windowing" is a very common technique used to minimize artifact. All the examples used in the present application first subtract any DC offset, and then use Hanning's method of windowing, which uses a cosine window to taper the original signal to zero amplitude at the edges. An example of the application of Hanning's method to raw EEG data is shown in FIG. 4. FIG. 5 shows the FFT of the EEG segment shown in FIG. 4. The gray line/area shows the raw FFT, which has a large number of points (2501), and is very noisy at higher frequencies. The black line shows the power density of the FFT at a selected, or spectrum averaged, set of 71 frequency bins. The power density at each frequency band or bin is the total integrated power in the frequency band or bin divided by the width of the frequency band or bin. There are many techniques, used under a variety of names for estimating or calculating the spectral content or average spectrum of a signal. These include: power spectral density estimation, periodograms, smoothed periodograms, wavelet transforms, spectrograms, and autoregressive moving average (ARMA) estimates, to name a few.

Figure 1:
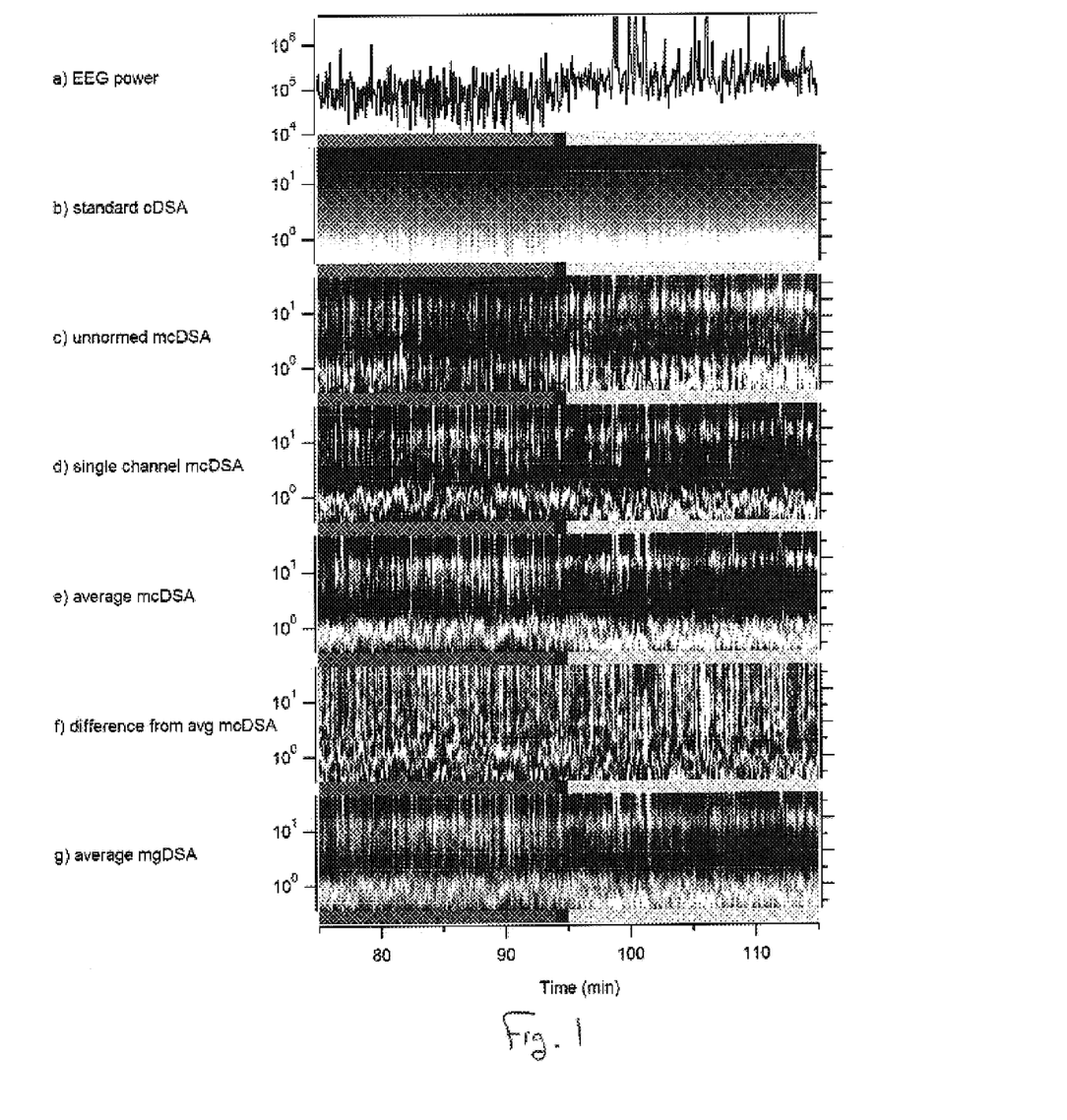
Figure 2:
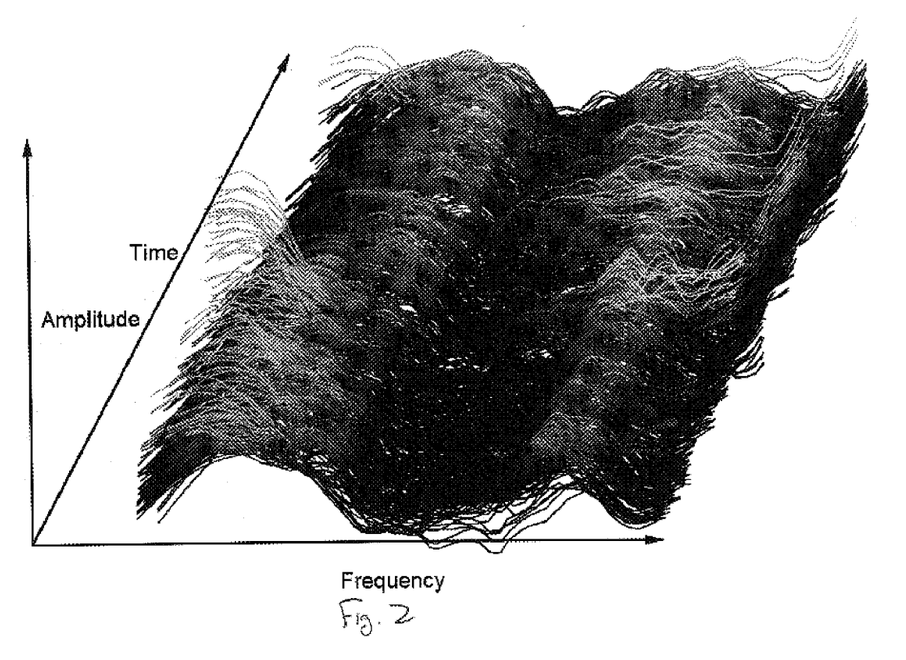
FIG. 2 shows the signal data from FIG. 1e) displayed using a modified compressed spectral array (mCSA) of the present application.
Figure 3:
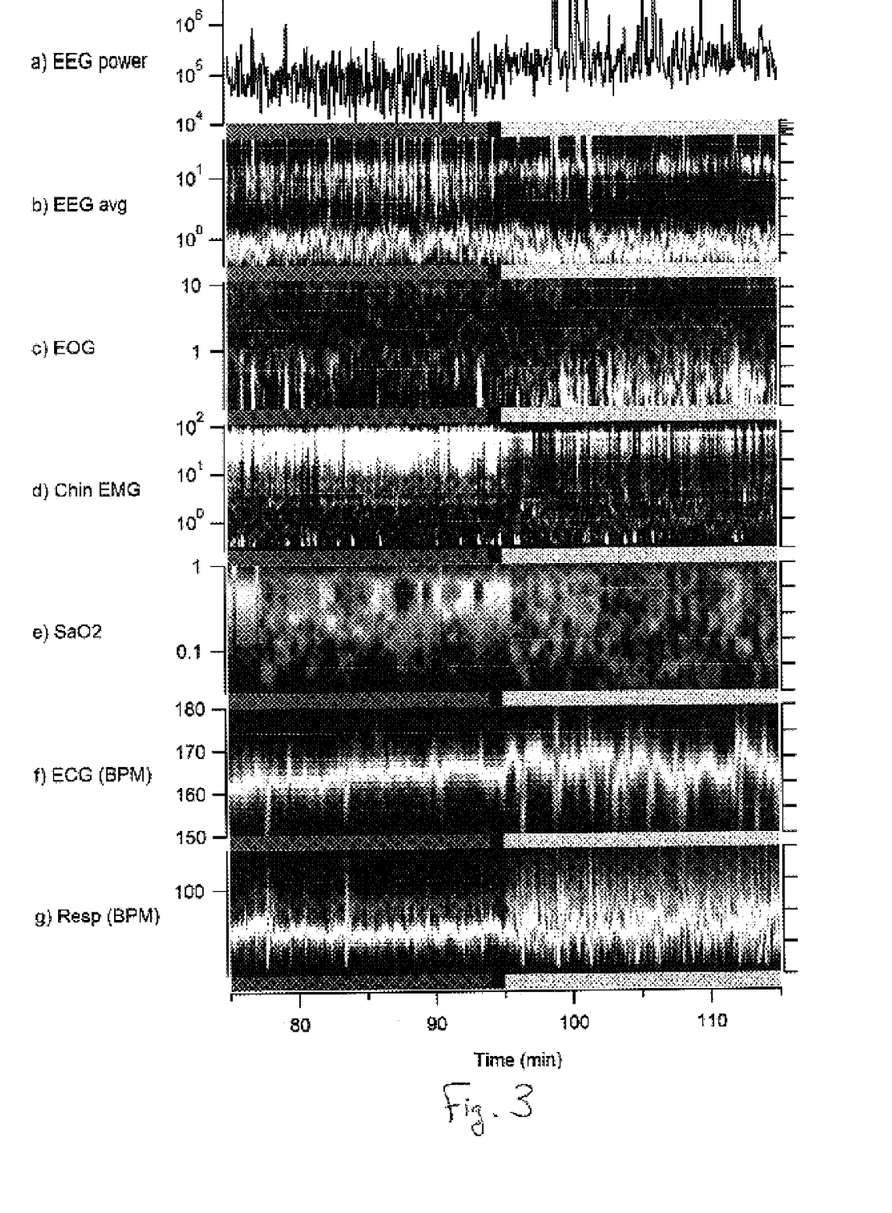
FIG. 3 shows additional complex biological signals using the mcDSA display technique of the present application, and specifically where 3a) is the same as 1a), 3b) is the same as 1e), 3c displays electroocular signals (EOG) from the eyes of a patient using the mcDSA of the present application, 3d) displays electromyographic signals (EMG) from the chin of a patient using the mcDSA of the present application, 3e) displays the spectral patterns of blood oxygenation or $SaO_2$ of a patient using the mcDSA of the present application, 3f) and 3g) displays the spectral changes in the electrocardiographic signals (ECG) and respiration or breathing patterns, respectively, of a patient using the mcDSA of the present application.
Figure 8:
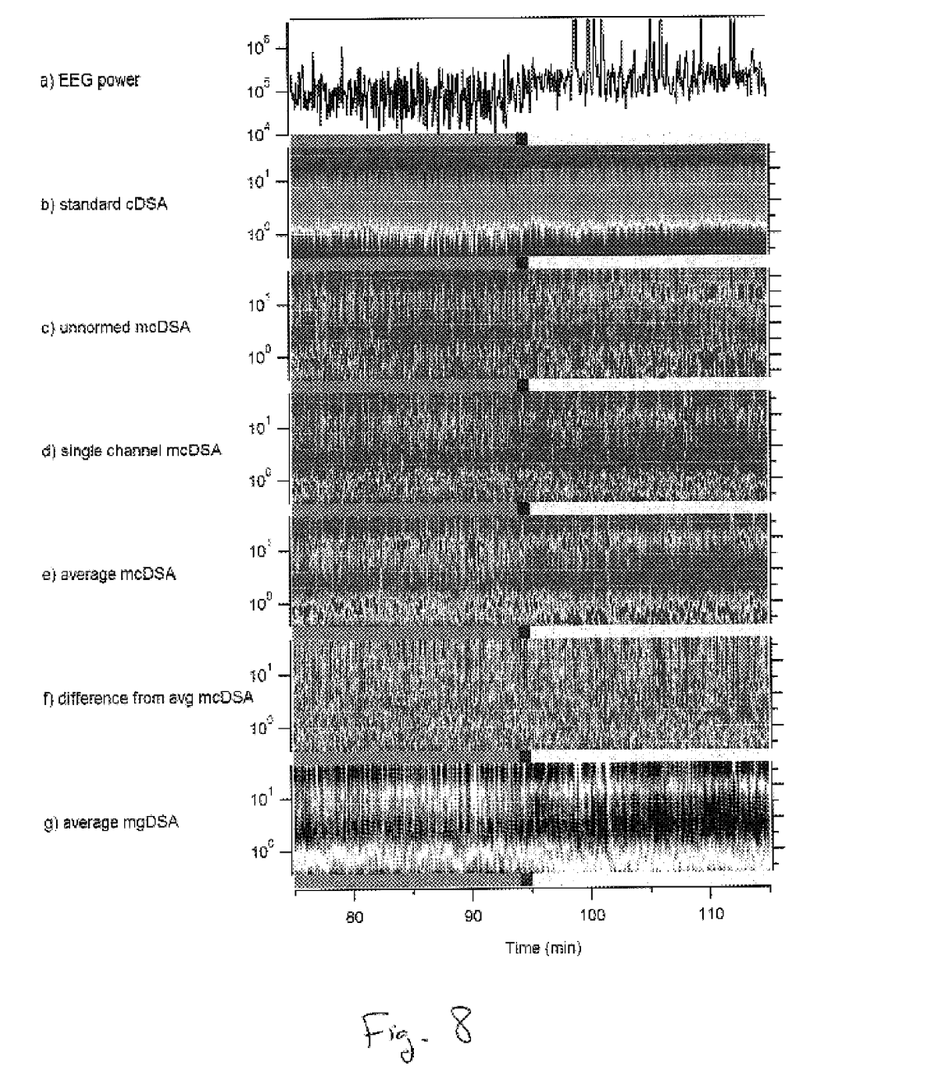

Further examples of conventional display techniques are provided in black and white in FIG. 1a) showing EEG power signal, and in FIG. 1b), which shows a black and white version of a standard color density spectral array (cDSA). Again, the cDSA maps the logarithm of the EEG power in each frequency bin and at each epoch or time to a color. FIGS. 8a) and 8b) provide the cDSA example of FIGS. 1a) and 1b) in color. It is noted that FIGS. 1 and 8 contain identical data, with FIG. 1 provided in black and white, and FIG. 8 in color. Likewise, the data in black and white FIG. 2 is identical to the color data in FIG. 9, and the black and white data in FIG. 3 is identical to the color data in FIG. 10.

The method of the present application is obtained and displayed using a computer system. The changes in spectral content of data signals over periods of time are displayed using a computer system. The method includes the steps of transforming time segments of digitized data signals into a frequency based spectral representation of the digitized data. Spectral data are then grouped into appropriate frequency bins. Each frequency bin is normalized by the frequency range of the bin. The energy or power in each frequency bin is then multiplied by $f^n$, where f is an estimate of the frequency of the bin, and n is an exponent used to normalize the frequency content of the data. A logarithmic value is then calculated for each frequency bin. The logarithmic value of each frequency bin for each time period is then mapped or assigned to a color or gray-scale value. Finally, the mapped color or gray-scale value is displayed on a computer monitor in the computer system as an image, where the signal frequency is represented along one axis, time is represented along a second axis, and the value of the energy or power at that given time and frequency is displayed as the color or gray-scale value assigned to that point Using the display method of the present application aids an observer to observe patterns and features in long term signal data more efficiently and quickly, where such patterns and features were previously difficult to observe due to long and tedious prior art data presentation techniques. These and other advantages and features of the method and system of the present application will be better understood from the detailed description of an embodiment of the system which is described in conjunction with the accompanying drawings.

BRIEF DESCRIPTION OF THE DRAWINGS

The patent or application file contains at least one drawing executed in color. Copies of this patent or patent application publication with color drawing(s) will be provided by the U.S. Patent Office upon request and payment of the necessary fee.

FIG. 1 shows a comparison of different graphed techniques or methods for displaying Density Spectral Arrays in black and white, and specifically with 1a) showing EEG power over time, 1b) showing standard Color Density Spectral Array, 1c) showing unnormalized signal data using the modified color density spectral array (mcDSA) of the present application, 1d) showing a single channel of EEG signal data using the mcDSA display of the present application, 1e) showing 6 channels of averaged signal data using the mcDSA display of the present application, 1f) showing the difference between the single channel and the 6 channel average using the mcDSA display of the present application and 1g) showing the averaged signal data in 1e), but displayed using a modified gray density spectral array (mgDSA) technique of the present application.

FIG. 8 shows a comparison of different graphed techniques or methods for displaying Density Spectral Arrays in color, and specifically with 8a) showing EEG power over time, 8b) showing standard Color Density Spectral Array, 8c) showing unnormalized signal data using the modified color density spectral array (mcDSA) of the present application, 8d) showing a single channel of EEG signal data using the mcDSA display of the present application, 8e) showing 6 channels of averaged signal data using the mcDSA display of the present application, 8f) showing the difference between the single channel and the 6 channel average using the mcDSA display of the present application, and 8g) showing the averaged signal data in 8e), but displayed using a modified gray density spectral array (mgDSA) technique of the present application.

DETAILED DESCRIPTION OF THE DRAWINGS

Figure 9:
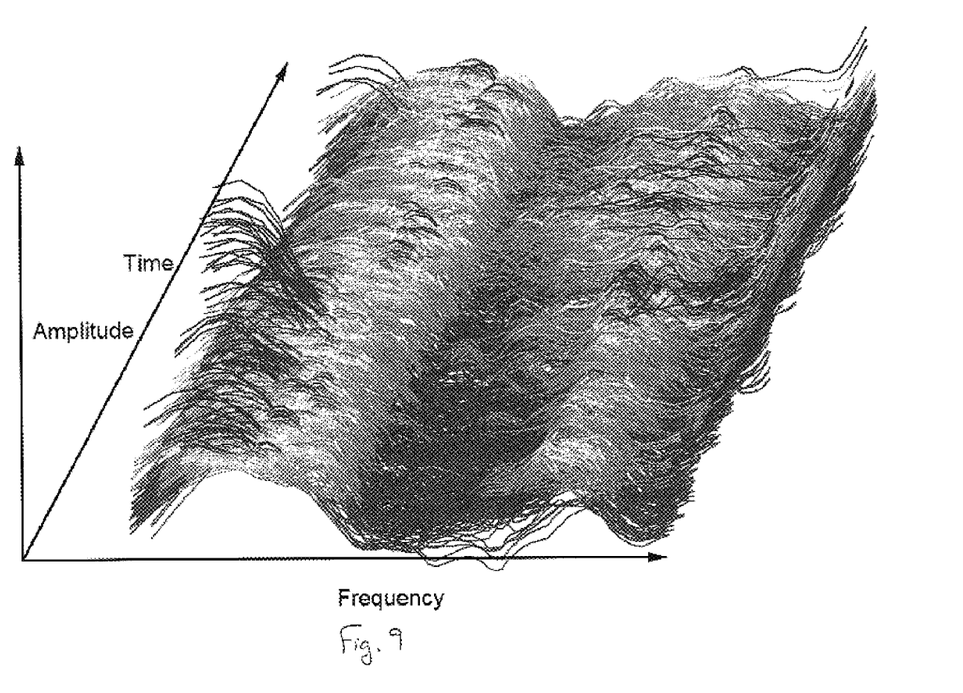
FIG. 9 shows the signal data from FIG. 8e) displayed in color using a modified compressed spectral array (mCSA) of the present application.
Figure 10:
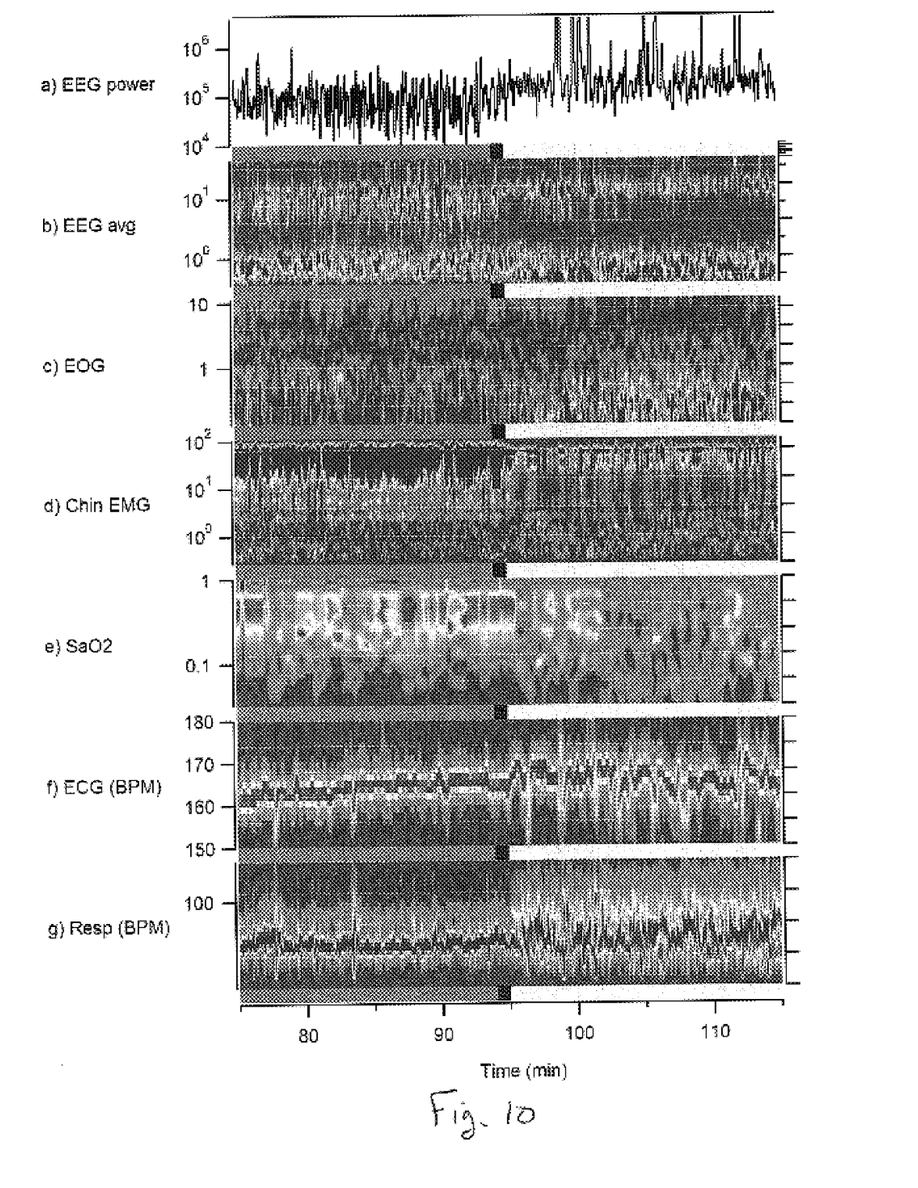
FIG. 10 shows additional complex biological signals using the mcDSA color display technique of the present application, and specifically where 10a) is the same as 8a), 10b) is the same as 8e), 10c) displays electroocular signals (EOG) from the eyes of a patient using the mcDSA of the present application, 3d) displays electromyographic signals (EMG) from the chin of a patient using the mcDSA of the present application, 10e) displays the spectral patterns of blood oxygenation or $SaO_2$ of a patient using the mcDSA of the present application, 10f) and 10g) displays the spectral changes in the electrocardiographic signals (ECG) and respiration or breathing patterns, respectively, of a patient using the mcDSA of the present application.
Figure 11:
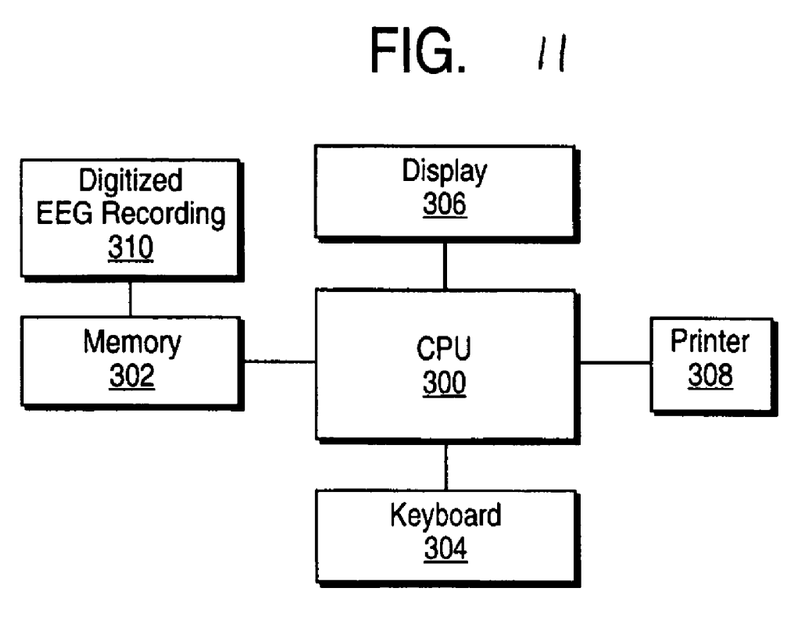
FIG. 11 schematically illustrates a computer system in which signal data may be recorded, provided to a computer memory, the method steps performed on the signal data within the central processing unit of the computer, manipulated as desired, displayed on a computer monitor and/or printed to an associated printer.

Turning now to black and white FIGS. 1 to 3 and color FIGS. 8 to 10, reproductions of the type that would be displayed on a computer monitor in a computer system as shown in FIG. 11 are provided. The graphs in FIGS. 1 to 3 and 8 to 10 illustrate the method for displaying spectral trends in complex signals. Specifically, FIGS. 1c) to 1g) show the display using the method developed for displaying the changes in spectral content of a signal over long periods of time.

As illustrated, the computer system includes a central processing unit (CPU) 300, a computer readable medium such as a memory 302, an input device such as a keyboard 304, and output devices such as a printer 308 and a display monitor 306 where the displays using the method of the present application may be viewed. The digitized signal recording, such as EEG, 310 is read into the memory 302 for processing by the CPU 300, which is capable of running a computer program code comprising instructions for performing the method steps and algorithms according to the present application.

To use the present method, data signals from a desires source are gathered and supplied to a computer system memory. The data signals are input, stored and manipulated as described below, using well known computer hardware and software systems.

The display is provided by first, transforming relatively short time segments, or epochs of digitized data, into frequency based spectral representations of the digitized data using one of many methods variously known under several names. Examples of methods which may be used include, fourier transforms, FFT, wavelet transforms, power spectral density, periodograms and spectrograms. Second, the resulting spectral energy or power data is grouped into frequency bins. Frequency bins represent all frequencies within a range of frequency, for example, 1 to 2 Hertz, which are appropriate for the signals of interest. Each frequency bin is normalized (or divided) by the range of the frequencies within its respective frequency bin (where $f_{high}$ minus $f_{low}$ provides the range). Third, the energy or power of the signal in each frequency bin is multiplied by $f^n$ (f raised to the power n), where f represents the geometric mean frequency or other reasonable estimate, or estimate, of the central frequency of the bin, and n is an exponent which is used to normalize the frequency content of the energy or power of the signal (frequently assigned but not limited to values such as 1, 1.5 or 2, for example).

Fourth, the logarithm (base 2, 10, natural, or any other preferred base) of the energy or power of the signal is calculated. Fifth, and optionally, the energy or power represented by each frequency bin may be normalized by the total energy or power of a single wider frequency band, thereby correcting for overall fluctuations in the amplitude of the signal. Sixth, the logarithmic value assigned to each frequency bin for each epoch of time is mapped to a color or gray-scale value and displayed as an image, where the signal frequency is represented along one axis, time or epoch number is represented along a second axis, and the value of the energy or power at that given time and frequency is displayed as the color or gray-scale assigned to that point.

The method described may be used for displaying spectral trends of any biological signals, including but not limited to:
a) Electroencephalographic signals (EEG) either as single (referential) channels, in single bipolar electrode pairs, or by averaging two or more of the signals obtained using the methods above immediately before the step of assigning a color or gray-scale mapping. The method may be used for any of many applications of EEG signals, including but not limited to, assessing sleep state, wakeful state, seizures, anesthesia monitoring, or coma monitoring. The method may be applied to EEG signals of patients of any age, including fetal, premature infants, neonatal infants, children, and/or adults, as well as animals.
b) Electrocardiographic signals (ECG) or heart rate or heart beat-to-beat interval data.
c) Respiratory signals obtained from various methods including chest or abdominal respiration bands, airflow sensors, airway temperature sensors, or airway pressure sensors.
d) Blood gas signals or blood oxygenation signals, for example, from a pulse oximeter.
e) Temperature signals including skin or core body temperature.
f) Continuous blood pressure signals.
g) Electromyographic signals (EMG) obtained from chin, face, chest, extremities, or any other areas of the body.
h) Electroocular signals (EOG) from electrical measurement of the eyes.
i) Body motion or position signals obtained from any of a number of sensors including accelerometers or extensible sensors.

The method above may also be used for displaying spectral trends of sound, especially to characterize the timbre or tone color of the sound, such as for voice, speech, music, and/or other environmental sounds. Non-biological complex signals may also make use of the present method of display, for example, for displaying stock market or other financial market valuation, weather related data, and/or other complex stochastic (random) processes that are otherwise difficult to characterize.

FIG. 1 shows several versions of DSA. All figures show the same forty minutes of EEG taken from a 5 day old, 32 week post-conceptional age premature infant (i.e. an infant born 8 weeks early). The first twenty minutes shows a period of quiet sleep which is generally characterized by an EEG pattern called Trace Discontinu and even regular breathing (see FIG. 6). The last twenty minutes shows a period of active sleep which is generally characterized by a different more continuous EEG pattern and irregular breathing (see FIG. 7). 1a) shows the overall relative power of the EEG within each epoch. 1b) shows the standard cDSA, which shows a fluctuating color pattern that generally follows the overall power shown in 1a. 1c) shows unnormalized (fifth step above skipped) mcDSA. In this graph which has had the 1/f trend removed, we can see more signal (red) near 1 and 10 Hz, with a definite change in the pattern comparing the left and right halves of the display. However, the display of the frequency spectrum is still amplitude dependant, as indicated by the vertical purple stripes in the left half. 1d) shows mcDSA for a single channel of EEG. 1e) shows the mcDSA averaged over six channels of EEG. With the averaged mcDSA the overall trend of frequencies is more apparent, with the low frequencies shifting down slightly in the last twenty minutes, the middle frequencies being absent (purple), and the upper frequency energy shifting upward slightly. 1f) shows the difference between the mcDSA of a single channel and the mcDSA of the six channel average. Although there no major trends in this example, this comparison can be very useful for highlighting when a channel is significantly different from the others. Finally, 1g) mgDSA is the same as 1e) mcDSA, but where levels of gray have been used in place of colors.

FIG. 2 shows the data from FIG. 1e displayed as modified compressed spectral array (mCSA) rather than modified color density spectral array (mcDSA). The color mapping is the same, but increasing frequency is toward the right, and most recent times are at the front.

Figure 6:
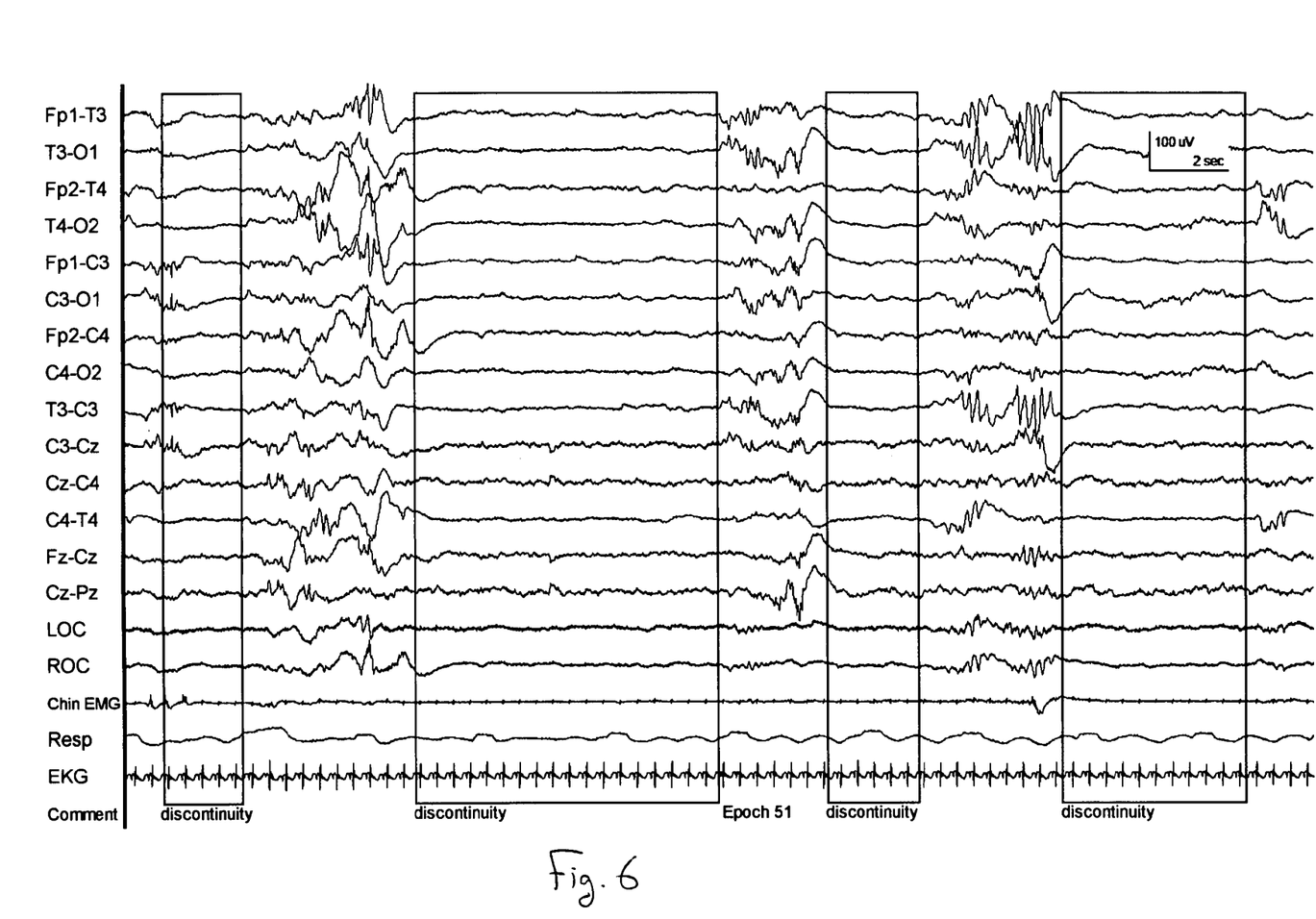
FIGS. 6 and 7 each show 20 second samples of the type of signals processed and displayed in FIG. 3 using the mcDSA of the present application, with FIG. 6 showing signal data from a patient in quiet sleep, and FIG. 7 showing signal data from the patient in active sleep.
Figure 7:
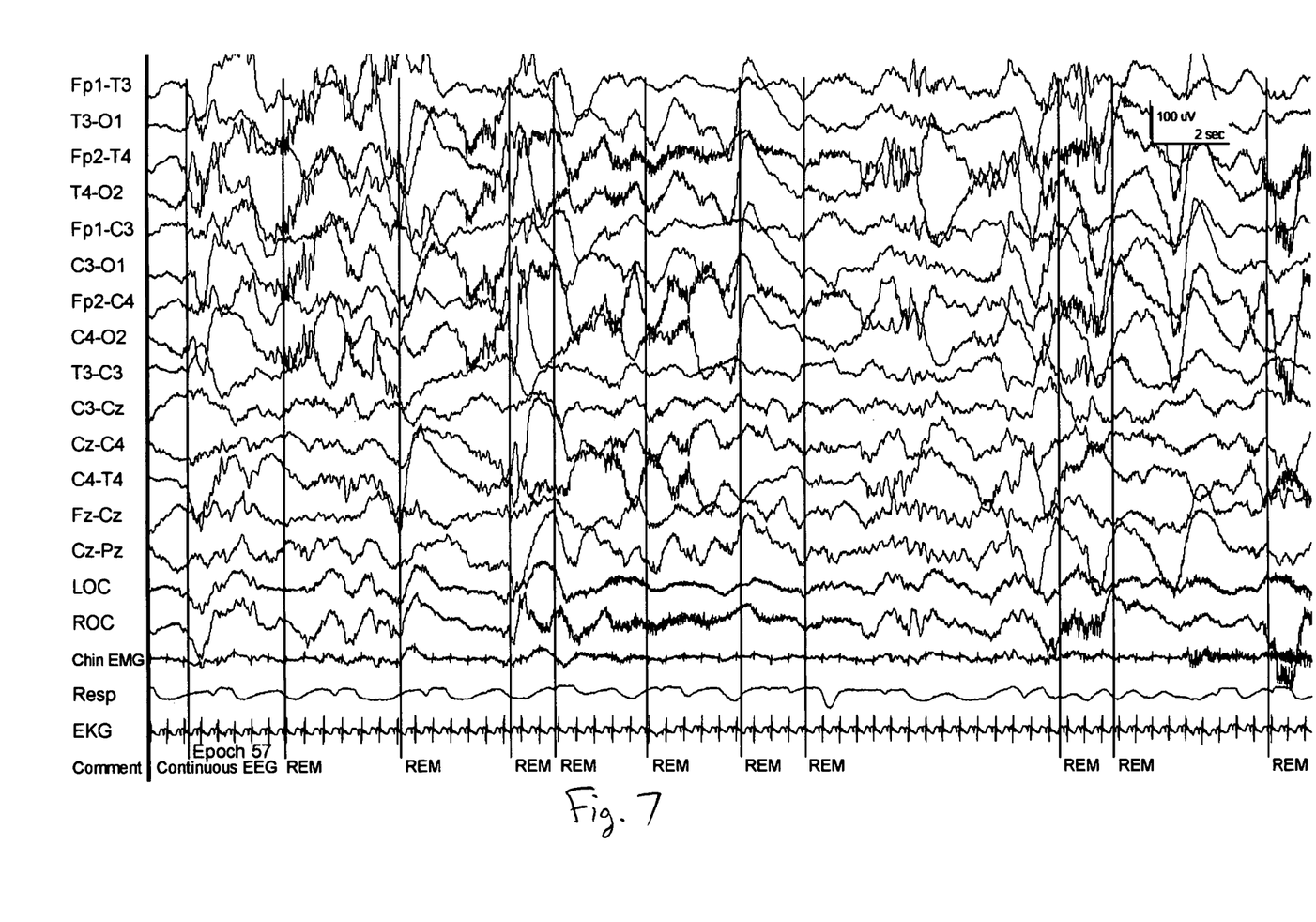

FIG. 3 shows the mcDSA for several different biological signals measured from the same infant and time period shown in FIG. 1. 3a) and 3b) are the same as 1a) and 1e), and show the EEG. 3c) shows EOG signals from the eyes. The left half of this mcDSA display shows the emergence of eye movements in the last twenty minutes as the red at the bottom of the trace. 3d) shows EMG from the chin, and shows a marked change in pattern between the left and right halves. 3e) shows the spectral patterns of blood oxygenation or $SaO_2$ and also shows marked differences between left and right halves. 3f) and 3g) shows the spectral changes in the heart rate and breathing patterns of the infant. During quiet sleep (left half) breathing and heart rate tend to be very even and steady as shown by a narrow red band. During active sleep (right half) breathing and heart rate become much more variable, with the reflected spectral change showing up as a much wider and more fluctuating band of energy. FIGS. 6 and 7 each show twenty second examples of the type of signals processed in FIG. 3. FIG. 6 shows quiet sleep, and FIG. 7 shows active sleep.

While exemplary embodiments of the complex signals which may be displayed using the method of the present have been described with a certain degree of particularity, it is the intent that the method of the present application include non-biological signals as well as biological signals and all modifications and alterations from the disclosed methodology falling within the spirit or scope of the appended claims.

I claim:

1. A method for displaying changes in spectral content of data signals over periods of time comprising the steps of:
   transforming time segments of digitized data signals into a frequency based spectral representation of the digitized data;
   grouping the resulting spectral data into appropriate frequency bins, with each frequency bin normalized by the frequency range of the bin;
   multiplying the energy or power in each frequency bin by $f^n$, where f represents an estimate of the frequency of the bin, and n is an exponent which is used to normalize the frequency content of the data;
   calculating a logarithmic value for each frequency bin;
   mapping the logarithmic value of each frequency bin for each time period to a color or gray-scale value; and
   displaying the mapped color or gray-scale value as an image, where the signal frequency is represented along one axis, time is represented along a second axis, and the value of the energy or power at that given time and frequency is displayed as the color or gray-scale value assigned to that point.

2. The method of claim 1 further comprising the step of normalizing the energy or power represented by each frequency bin by the total energy or power of a single wider frequency band to correct for overall fluctuations in the amplitude of the signal.

3. The method of claim 1, wherein the frequency based spectral representation of data is displayed as a modified compressed spectral array (mCSA), with frequency increasing along one axis and time increasing along a second axis.

4. A method for displaying changes in spectral content of data signals over periods of time on a computer system comprising the steps of:
   transforming, in a computer system, time segments of digitized data signals gathered from a desired source into a frequency based spectral representation of the digitized data;
   grouping the resulting spectral data into appropriate frequency bins, with each frequency bin normalized by the frequency range of the bin;
   multiplying the energy or power in each frequency bin by $f^n$, where f represents an estimate of the frequency of the bin, and n is an exponent which is used to normalize the frequency content of the data;
   calculating a logarithmic value for each frequency bin;
   mapping the logarithmic value of each frequency bin for each time period to a color or gray-scale value; and
   displaying in a computer system monitor the mapped color or gray-scale value as an image, where the signal frequency is represented along one axis, time is represented along a second axis, and the value of the energy or power at that given time and frequency is displayed as the color or gray-scale value assigned to that point.

* * * * *